United States Patent [19]

Hogan

[11] Patent Number: 4,885,000
[45] Date of Patent: Dec. 5, 1989

[54] ISOLATION, STERILIZATION AND MAXIMUM OBSERVATION TENT

[75] Inventor: John D. Hogan, Gloucester, Mass.

[73] Assignee: The Beth Israel Hospital Association, Boston, Mass.

[21] Appl. No.: 142,077

[22] Filed: Jan. 8, 1988

Related U.S. Application Data

[63] Continuation-in-part of Ser. No. 1,648, Jan. 9, 1987, abandoned.

[51] Int. Cl.$^4$ .............................................. A61M 16/02
[52] U.S. Cl. .................................................. 600/21; 312/1
[58] Field of Search .................. 600/21, 22; 128/846, 128/869, 870, 897, 205.26; 312/1, 3–6; 5/60, 414; 98/115.1–115.4

[56] References Cited

U.S. PATENT DOCUMENTS

| | | | |
|---|---|---|---|
| 1,977,386 | 10/1934 | Holes | ................................ 98/115.3 |
| 3,272,199 | 9/1966 | Mathews . | |
| 3,364,928 | 1/1968 | Creager et al. . | |
| 3,492,987 | 2/1970 | Parker . | |
| 4,224,936 | 9/1980 | Cox . | |
| 4,275,719 | 6/1981 | Mayer . | |
| 4,335,712 | 6/1982 | Trexler . | |
| 4,367,728 | 1/1983 | Mutke . | |
| 4,598,487 | 7/1986 | McAllester . | |
| 4,675,923 | 6/1987 | Ashley . | |
| 4,736,762 | 4/1988 | Wayman | ........................ 128/205.26 |

FOREIGN PATENT DOCUMENTS 1506930 12/1967 France .
1604033 12/1981 United Kingdom .

OTHER PUBLICATIONS

Human Pathology, vol. 17, No. 12 (Dec. 1986) pp. 126–127, "Autopsy Removal of the Brain in Aids: A New Technique".

Primary Examiner—Stephen C. Pellegrino
Assistant Examiner—Ralph Lewis
Attorney, Agent, or Firm—Lorusso & Loud

[57] ABSTRACT

An isolation, sterilization and maximum observation (ISMO) tent for the isolation of a corpse during a medical procedure and to contain matter spilling from the corpse. The ISMO tent includes a frame and a form fitted translucent sheet supported by the frame, and will preferably have a continuous elastic band secured to the bottom edge of the sheet and an absorbent material, treated with disinfectant, in close proximity thereto to prevent spillage of infectious material.

10 Claims, 4 Drawing Sheets

ISOLATION, STERILIZATION AND MAXIMUM OBSERVATION TENT

CROSS REFERENCE TO RELATED APPLICATION

This application is a continuation-in-part Application of prior pending application U.S. Ser. No. 001,648, filed Jan. 9, 1987, now abandoned entitled "AN ISOLATION, STERILIZATION AND MAXIMUM OBSERVATION TENT", the teachings of which are incorporated by reference.

BACKGROUND OF THE INVENTION

This invention relates to a device for the isolation of a body or a part of the body in a sterile environment and more particularly, this invention relates to device for the isolation of a corpse during and after the performance of an autopsy to prevent possible infection and contamination of medical personnel.

In many medical procedures, it is desirable to isolate the body of the patient. Isolation is important to protect a patient from microorganisms in the general environment. Patient isolation is also extremely important in the treatment of a patient suffering from a highly infectious disease for the safety of attending medical personnel.

In the case of an autopsy, isolation of the corpse is extremely desirable to protect the doctors and attendants during the autopsy, especially when a lethal and possibly contagious disease was the cause of death. Isolation could be important when AIDS, Jacob Creutzfeld disease, Hepatitis or Tuberculosis, for example, was the cause of death.

Furthermore, once the autopsy has been performed, infection of personnel can occur during the clean-up process. Blood spills, pieces of tissue and other fluids and matter associated with the autopsy can soil personnel clothing and the equipment and floors in the autopsy suite creating a risk of infection to personnel. Indeed, even the air surrounding the corpse may be infected with air-born microorganisms creating a health risk. Thus, personnel performing the autopsy are at risk during the autopsy and furthermore, personnel involved with the clean-up of the autopsy suite and the transport of items used during the autopsy are also in danger of infection. It has become apparent that equipment and procedures should be utilized during the autopsy that minimize the risk of spread of possible infection from the corpse. Therefore, it would be desirable to have an isolation apparatus surrounding the corpse to contain body matter, prevent microorganisms from becoming air-born and to provide a convenient and safe method to remove the matter during the clean-up after the autopsy. It would also be desirable to have a means for disinfecting the air within such an isolation apparatus after the autopsy has been performed and before the isolation is broken by removing the corpse from the isolation device.

Various devices have been suggested to isolate a body and to contain body matter while procedures are performed on the body. For example, U.S. Pat. No. 4,224,936 to Cox discloses a transit isolator that facilitates the transfer of a patient from one unit to another. The isolator comprises two sets of frames, one of which has suspended from it, an isolator in the form of a flexible film envelope and a basal structure to support the patient and all horizontal members. Essentially, this device is for the protection of a hypersensitive patient and would not contain matter secreted from the body of the patient. Moreover, it would not allow attending personnel to work on the patient without removing him from isolation.

U.S. Pat. No. 4,367,728 to Mutke discloses an isolation apparatus comprising a flexible envelope divided into a plurality of sealed sections having air or gas supplied so that optimum inflation condition of the sack is always achieved. It should be noted that this device is optimally a device for treatment of live patients. Furthermore, it requires air or gas systems for the good of the patient and to maintain isolation compartments.

Prior to the present invention there simply was no apparatus which could effectively protect medical personnel from contamination during an autopsy, provide a means for safe disposal of contaminated materials utilized during the autopsy and also disinfect the air after the autopsy had been performed.

Accordingly, it is a principal object of the present invention to provide a simple and inexpensive apparatus to isolate a corpse or part of the corpse from its surroundings during a medical procedure such as an autopsy so that medical personnel performing the medical procedure are protected from infectious matter.

A further object of the present invention is to provide an isolation apparatus which will reduce the risk of infection to physicians and other attending personnel during and after a medical procedure.

Another object of the present invention is to provide an isolation apparatus which is collapsible into its own self-contained disposable bag thereby allowing the apparatus and any corpse matter resulting from the medical procedure which had been performed to be disposed of with minimum risk of spread of infection.

Yet another object of the present invention is to provide an isolation apparatus having means for disinfecting the air within the isolation apparatus after the medical procedure is completed an before the isolation seal is broken.

Still another object of the present invention is to provide an isolation apparatus having means for collection and containment of body matter and fluids secreted during a medical procedure.

SUMMARY OF THE INVENTION

The present invention provides a simple and inexpensive isolation apparatus which will isolate a corpse during a medical procedure such as an autopsy and contain matter spilling from the corpse during the procedure that may be infectious.

Doctors and attendants performing the medical procedure are then protected both during and after the procedure and through the clean-up and sterilization process.

The isolation, sterilization and maximum observation (ISMO) tent of the present invention comprises a frame and a one-piece form fitted translucent sheet supported by the frame. The ISMO tent of the present invention may be sized to fit a whole corpse on which the medical procedure will be performed. In a preferred embodiment, the bottom edges of the tent have a continuous elastic band secured thereto, similar to the elastic band on a shower cap, so that when the tent is placed on an operating table the elastic band draws the edges of the tent under the table so that any liquids that might otherwise spill and reach the floor of the operating room are trapped by the tent itself. In a preferred embodiment, there is an adsorbent material, treated with disinfectant, in close proximity to the bottom edge of the tent to adsorb any fluids that may be trapped by the pocket formed by the elasticized edges of the tent.

Important features of the present invention are those features designed to reduce or eliminate the risk of spread of contagious diseases. Thus, the tent itself completely encloses the corpse and has portholes which are sealably released when a hand is pushed through to allow an attendant to perform the autopsy. The tent will have one or more slits or openings releasably sealed with flaps that can be opened for removal of organs and/or insertion of instruments. The tent is provided with an extended rear panel comprising a disposable bag, sealable with a flap, so that at the end of the procedure, the entire tent and even the frame may be collapsed into the bag and sealed with the flap for easy and sanitary disposal of the device. In addition, along the top of the side walls of the tent, one or more atomizers are placed for decontaminating sprayers which can be activated after the medical procedure to decontaminate all air-born, ambient particles and gases before the isolation seal is broken and the corpse is removed.

The invention will be more clearly understood from a reading of the following detailed description of the invention taken together with the drawing in which like reference numbers refer to like members throughout the various figures.

DESCRIPTION OF THE PREFERRED EMBODIMENTS

At the outset, the invention is described in its broadest overall aspects with a more detailed description following.

The isolation, sterilization and maximum observation (ISMO) tent of the present invention is comprised of a frame and a one piece form fitted sheet supported by the frame. The frame for the ISMO tent is comprised of various interlocking parts. The frame may be formed of any material capable of supporting the tent. Suitable materials are aluminum, steel or even hard plastic. If it is desired that the frame be disposable along with the tent, an inexpensive material may be used to form the frame and the frame will be provided with hinges or telescopic fittings or any suitable means so that the frame can fold into itself for compact disposal. Should it be desirable to have a permanent frame, the frame can attach to either the floor, the ceiling, or the table.

The ISMO tent of the present invention may be made for a procedure involving the whole body or merely a portion of the body. A whole body tent is useful when an autopsy is being performed. A half body tent would be used when the medical personnel are examining only a portion of the body, for example the head when a patient has died from a brain disorder or from a head injury. The structure of the ISMO tent of either embodiment is similar, except that the whole body ISMO tent will be sized and structured to surround the whole corpse.

Figure 1:
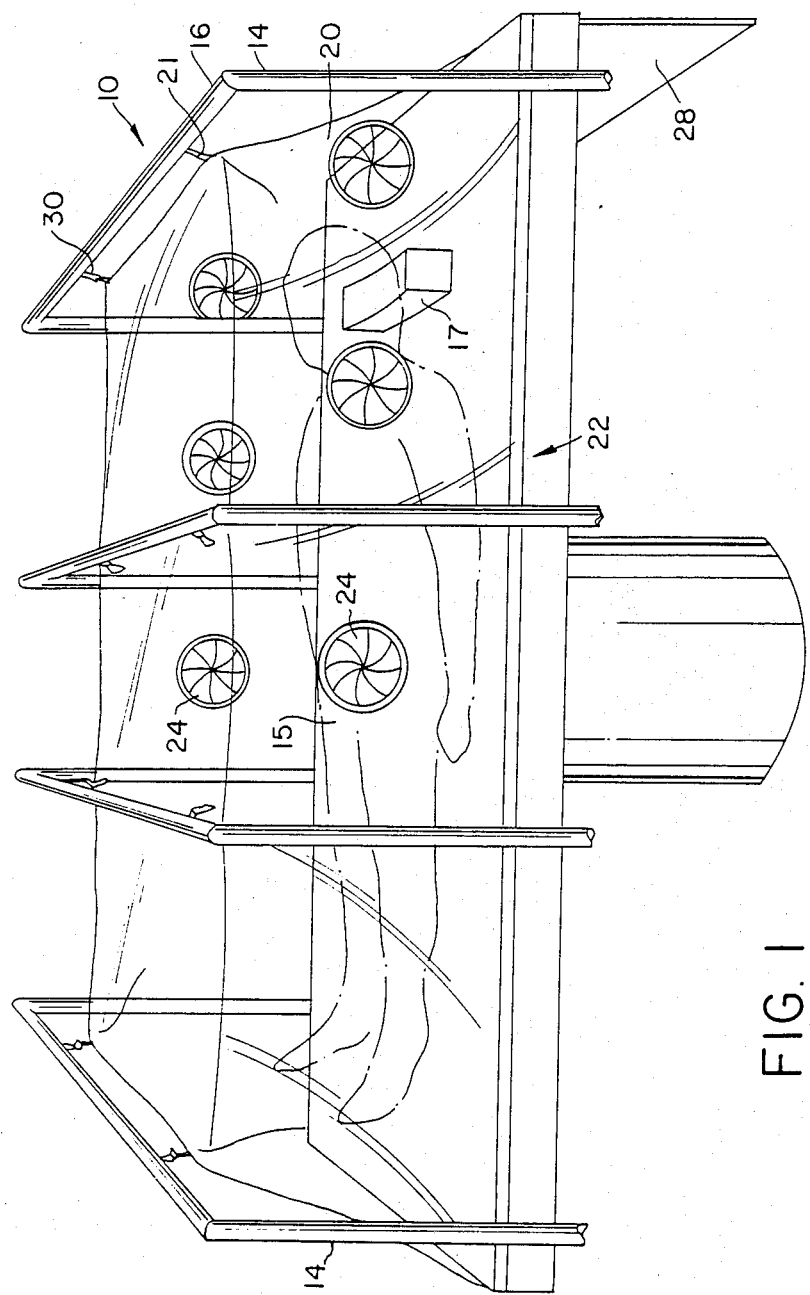
FIG. 1 is a perspective view of a full corpse isolation, sterilization and maximum observation tent in accordance with the present invention.

FIG. 1 illustrates the whole body ISMO tent. A preferred embodiment of the frame is shown in FIG. 1, the frame comprises vertical posts 14 that can be attached to either the table 22, or the floor, or even the ceiling. The frame may consist of horizontal members 16 depending on the materials used to make the frame. The frame has hooks 30 that coincide with the location of the loops 21 on the tent. There is an elastic band 48 attached o three sides near the bottom edge of the tent that pulls the bottom edge of the tent under the table thereby sealing the tent against the edges of the table. An adsorbent material that may be treated with a disinfectant aids in sealing the tent to the edge of the table and adsorbs any fluids that may collect along the edge of the table.

Figure 3:
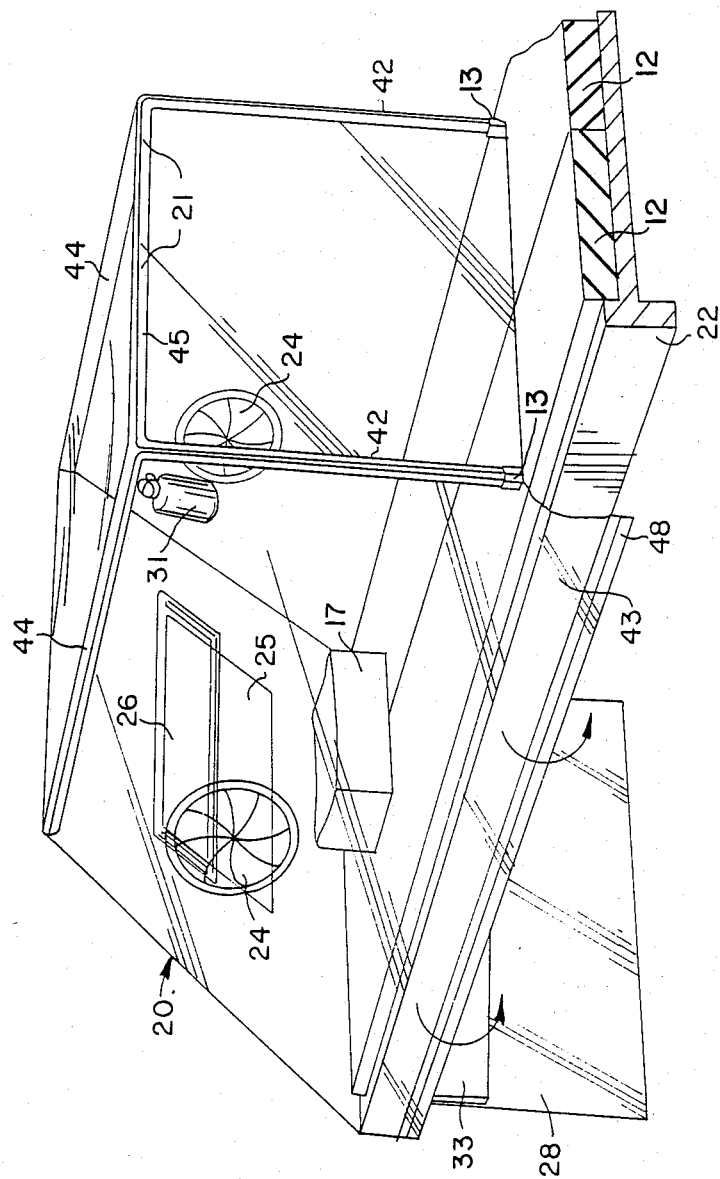
FIG. 3 is a perspective view of a half corpse isolation, sterilization and maximum observation tent in accordance with the present invention.

FIG. 3 illustrates the half body ISMO tent. The frame for the half body ISMO tent consists of vertical members 42 and can have horizontal members 45 as well. The body or half body rests on table pads 12 which are supported by the table 22. Frame supports 13 are provided to hold the frame 21 on the table pads 12. In either embodiment, a headrest 17 may be provided for the corpse.

The tent 20 for both the whole and half corpse ISMO is a one piece, clear, flexible sheet that is supported by the frame. The tent may hang from the frame by plastic attachment loops 21 which are attached to the tent 20. The flexible tent may be formed from any material which will allow viewing through the tent. Therefore, any transparent air-tight material, such as a flexible plastic or polyurethane would be suitable in the present invention. The whole corpse and half corpse ISMO tents of the present invention are substantially identical except for their lengths.

Figure 4:
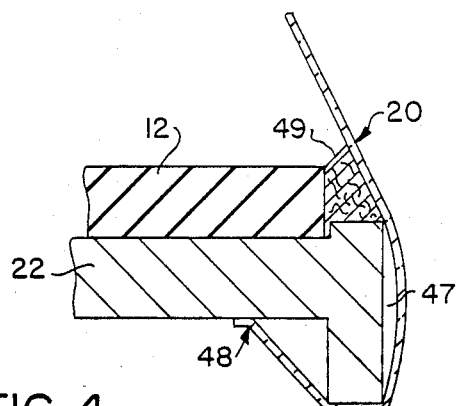
FIG. 4 is a schematic diagram of the edge seal and fluid collector of the isolation, sterilization and maximum observation tent and its attachment to the support or table on which the corpse rests in accordance with the present invention.

The ISMO tent of the present invention is designed with numerous features which will maintain isolation during the autopsy and prevent the spread of infection during and after autopsy. The tent sides are designed to be long enough to extend past the bottom of the table as the tent is supported by the frame. FIG. 4 shows the sides of the tent securely held in place by the elasticized edge 48 of the tent to the underside of the table. As shown in FIG. 3, the sides of the tent drape over the edges of the table 22 on which the corpse rests, then are tucked under the edge, in the direction of the arrows in this figure, and are held in place under the table by an elastic edge 48 pulling tight.

FIG. 4 illustrates the liquid seal and securing system of the tent sides. In FIG. 4, it can be seen that when the ISMO tent drapes over the sides of the table, the liquid seal 49, which may consist of an adsorbent material, is pulled tightly against the side of the table 22. The table 22 may support table pad 12 on which the corpse rests.

Figure 5:
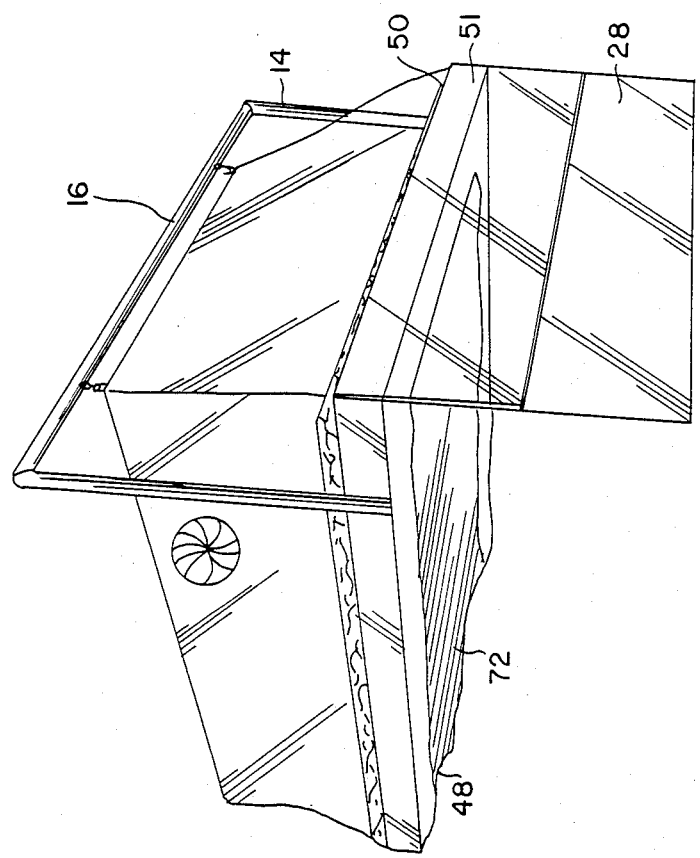
FIG. 5 is a perspective view of an isolation, sterilization and maximum observation tent showing its attachment to the table or support in accordance with the present invention.

FIG. 5 further illustrates the liquid sealing mechanism for securing the tent to the table. The adsorbent material 50 is located all along the outer edge of the tent. Below this adsorbent strip 50 is the elastic band 48 attached to three sides of the tent 20. An adhesive strip 51 is located on the front edge of table 20 and seals the front edge of the tent. The other three sides of the tent are pulled tightly against the table. Any liquid on or near the edges of the table is thereby adsorbed and disinfected by the adsorbent strip 50.

Figure 2:
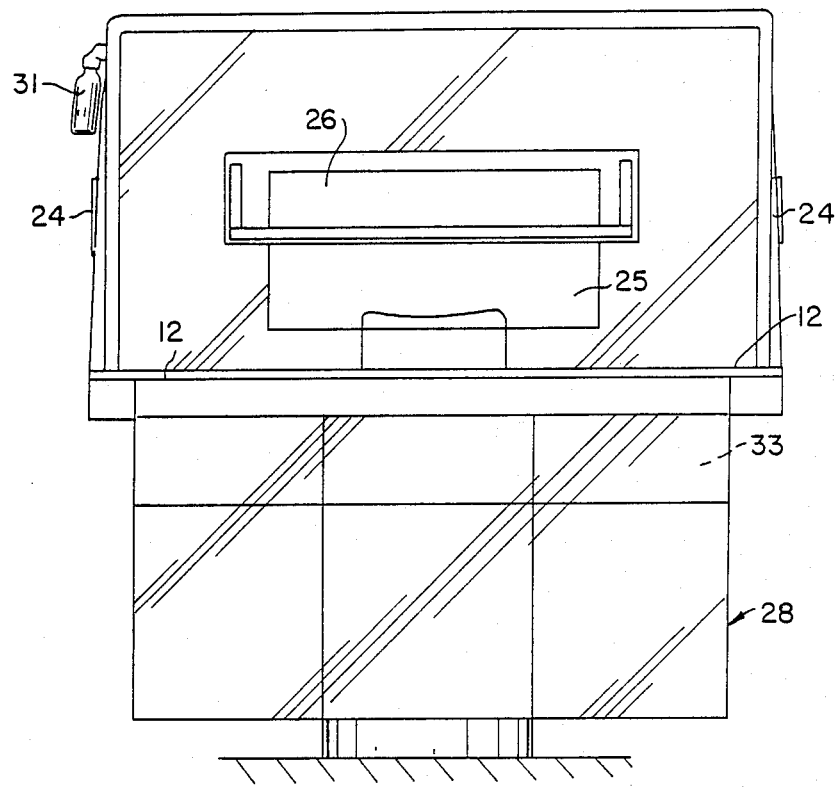
FIG. 2 is a left side view of an isolation, sterilization and maximum observation tent in accordance with the present invention.

FIG. 2, which shows a left side view from behind the head of the patient within either the half corpse or whole corpse ISMO tent, illustrates other safety features. The tent 20 has aperture type expanding portholes 24 for the doctor's and technician's access to the corpse. Aperture type is meant that the portholes are sealed prior to the insertion of a hand or object therethrough. Upon their insertion, the opening of the porthole 24 unfolds to permit the object to go through, but will still maintain a seal to prevent microorganisms from inside the tent from escaping into the environment. The portholes may additionally be provided with gloves for the medical personnel. The portholes may be placed anywhere along the tent that it is envisioned access to the corpse will be required. These portholes 24 enable access to the corpse while maintaining isolation between the attendants and the corpse.

The tent may have one or more small sealable portholes or pockets 25 sealable with a flap 26 communicating with the interior of the tent to allow insertion of instruments into the tent 20. One embodiment of this pocket 25 and flap 26 is shown more clearly in FIG. 2 in a place it can be positioned. The pocket 25 can be positioned anywhere on the tent 20 for the convenience of the attendants. For example, the rear of the tent 20 may also have a pocket 25 and a sealable flap 26 that is able to be opened and closed, for example by a velcro seal, for the removal of organs. This configuration is shown in FIG. 3. The flap 26 can be sealed with means such as velcro strips and will maintain the isolation in the ISMO tent until it is released and an object pushed through into or out of the pocket 25.

The features which will maximize prevention of the spread of infection are the atomizers 31 and the disposal bag 28. Along the top of the sides of the tent and in communication with the interior of the tent are one or more atomizers 31 and the disposal bag 28. Along the top of the sides of the tent and in communication with the interior of the tent are one or more atomizers 31 for decontaminating sprays which can be activated after the procedure to decontaminate all air-born, ambient particles or gases inside the tent before removal of the corpse 15 from the tent 20. Conventional atomizers, such as those used in the funeral industry may be incorporated into the present invention.

The disposal bag 28 is located at the rear of the tent. The tent 20 has an extended rear pocket which forms a disposal bag 28 that is attached to the rear of the table. At the end of the procedure, the entire tent may be collapsed into the bag 28 for easy and sanitary disposal of the tent and the corpse matter contained therein. The disposal bag is then sealed by suitable means. This allows for completely sanitary disposal of the fluids and remains incorporated therein.

It is understood that the form of the isolation, sterilization and maximum observation tent shown and described herein is a preferred embodiment and that the device may be constructed of various other materials without departing from the spirit and scope of the invention. The invention is defined as all embodiments within the scope of the claims which follow.

What is claimed is:

1. An isolation, sterilization and maximum observation apparatus for examination of a corpse resting on a table or support comprising:
   (a) a frame;
   (b) a disposable tent, having a plurality of sides supported by said frame, fabricated of transparent, air-tight material comprising:
      (i) means located on said tent to access the interior of said tent while preventing the escape of any materials within said tent;
      (ii) means located on said tent and in communication with the interior of said tent to decontaminate air-born, ambient, contagious particles located within said tent;
      (ii) a sealable disposable bag located along an edge of a base of said tent extending substantially along the length of one of said plurality of sides in which said tent and frame may be collapsed and contained therein said disposable bag being sanitarily sealable; and
      (iv) liquid sealing means, secured on said tent, positioned so that when said tent is draped over the table said liquid sealing means is pulled tightly against the table or support.

2. The apparatus of claim 1 wherein said tent is supported by said frame by loops which are attached to said tent and allow said tent to hang from the frame.

3. The apparatus of claim 1 wherein said tent hangs under said frame and is therefore supported by said frame.

4. The apparatus of claim 1 wherein the means to access the interior of said tent are aperture type portholes.

5. The apparatus of claim 1 wherein the means to access the interior of said tent are sealable pockets which allow for insertion of instruments into the interior of the tent and for the removal of tissues and organs.

6. The apparatus of claim 1 wherein the means to decontaminate air-born, ambient contagious particles located within said tent are one or more atomizers for decontamination sprays in communication with the interior of said tent which will be actuated prior to the removal of the corpse.

7. The apparatus of claim 1 further comprising:
   one or more table pads to protect the table and which are secured by the weight of the body;
   wherein said frame comprises vertical, overhanging and crosspoles defining boundaries of a rectangular box; and
   means to secure said frame to a table.

8. The apparatus of claim 1 further comprising:
   an adhesive strip for placement on a front edge of the table; and
   wherein said liquid sealing means further comprises an elastic band positioned on an outer edge of three sides of said tent such that when the outer edge of said tent is drawn under the table said tent is pulled tightly against said table and the fourth side of said tent is tightly secured against the table by attaching it to said adhesive strip.

9. The apparatus of claim 8 wherein said sealing means further comprises a strip of absorbent material positioned along the outer edge of said tent.

10. The apparatus of claim 9 wherein said absorbent material is treated with disinfectant.

* * * * *